(12) United States Patent
Wilmer et al.

(10) Patent No.: US 11,513,100 B2
(45) Date of Patent: Nov. 29, 2022

(54) GAS SENSOR AND METHOD OF OPTIMIZING AN ARRAY OF GAS SENSORS

(71) Applicants: UNIVERSITY OF PITTSBURGH-OF THE COMMONWEALTH SYSTEM OF HIGHER EDUCATION, Pittsburgh, PA (US); UNITED STATES DEPARTMENT OF ENERGY, Washington, DC (US)

(72) Inventors: Christopher E. Wilmer, Pittsburgh, PA (US); Jenna Gustafson, Pittsburgh, PA (US); Paul R. Ohodnicki, Allison Park, PA (US); Jagannath Devkota, Pittsburgh, PA (US)

(73) Assignees: University of Pittsburgh-Of the Commonwealth System of Higher Education, Pittsburgh, PA (US); United States Department of Energy, Washington, DC (US)

( * ) Notice: Subject to any disclaimer, the term of this patent is extended or adjusted under 35 U.S.C. 154(b) by 572 days.

(21) Appl. No.: 16/479,675

(22) PCT Filed: Jan. 26, 2018

(86) PCT No.: PCT/US2018/015392
§ 371 (c)(1),
(2) Date: Jul. 22, 2019

(87) PCT Pub. No.: WO2018/140696
PCT Pub. Date: Aug. 2, 2018

(65) Prior Publication Data
US 2021/0404989 A1 Dec. 30, 2021

Related U.S. Application Data

(60) Provisional application No. 62/451,090, filed on Jan. 27, 2017.

(51) Int. Cl.
*G01N 29/02* (2006.01)
*B01J 20/22* (2006.01)
*G01N 33/00* (2006.01)

(52) U.S. Cl.
CPC .......... *G01N 29/022* (2013.01); *B01J 20/226* (2013.01); *G01N 33/004* (2013.01);
(Continued)

(58) Field of Classification Search
CPC ........... G01N 29/022; G01N 2291/021; G01N 2291/0256; G01N 2291/0423;
(Continued)

(56) References Cited

U.S. PATENT DOCUMENTS 8,480,955 B2 7/2013 Yaghi et al.
9,329,154 B1 5/2016 Allendorf et al.
(Continued)

OTHER PUBLICATIONS

Yamagiwa et al, 'Detection of Volatile Organic Compounds by Weight-Detectable Sensors coated with Metal-Organic Frameworks', Scientific Reports, vol. 4, article No. 6247, Sep. 1, 2014 (Sep. 4, 2014), p. 1-6.
(Continued)

*Primary Examiner* — Suman K Nath
(74) *Attorney, Agent, or Firm* — Philip E. Levy; Eckert Seamans Cherin & Mellott LLC

(57) ABSTRACT

A gas sensor (100,200) includes at least one sensor device including a surface acoustic wave (SAW) device (110) or a quartz crystal microbalance (QCM) device (210), and a layer of metal organic framework (MOF) material (120,220) disposed on each of the at least one sensor device. The at least one sensor device is structured to sense a change in mass of the MOF material.

13 Claims, 15 Drawing Sheets

(52) U.S. Cl.
CPC .................. *G01N 2291/021* (2013.01); *G01N 2291/0256* (2013.01); *G01N 2291/0423* (2013.01); *G01N 2291/0426* (2013.01); *G01N 2291/106* (2013.01)

(58) Field of Classification Search
CPC ..... G01N 2291/0426; G01N 2291/106; G01N 33/004; B01J 20/226
See application file for complete search history.

(56) References Cited

U.S. PATENT DOCUMENTS

| | | | |
|---|---|---|---|
| 9,546,887 B1 * | 1/2017 | Talin | .................... G01N 29/032 |
| 2015/0192548 A1 | 7/2015 | Wilkinson et al. | |

OTHER PUBLICATIONS

Carey et al, 'Selection of Adsorbates for Chemical Sensor Arrays by Pattern Recognition', Analylical Chemistry, vol. 58, No. 1, Jan. 31, 1986 (Jan. 31, 1986), p. 149-153.

Tu et al, 'Engineering Zeolitic-lmid,uolate Framework (ZIF) Thin Film Devices for Selective Detection of Volatile Drganic Compounds', Advanced Functional Materials, vol. 25, Jun. 12, 2015 (Jun. 12, 2015), p. 4470-4479.

Gustafson et al, 'Computational Design of Metal-Organic Framework Arrays for Gas Sensing: Influence of Array Size and Composition on Sensor Performance' Journal of Physical Chemistry C, vol. 121, Feb. 6, 2017 (Feb. 6, 2017), p. 6033-6038.

Karra et al, 'Molecular Simulations and Experimental Studies of CO2, CO, and N2 Adsorption in Metal-Organic Frameworks', Journal of Physical Chemistry C, vol. 114, Aug. 25, 2010 (Aug. 25, 2010), p. 15735-15740.

* cited by examiner

GAS SENSOR AND METHOD OF OPTIMIZING AN ARRAY OF GAS SENSORS

CROSS-REFERENCE TO RELATED APPLICATIONS

This application is a U.S. National Stage Application under 35 U.S.C. § 371 of PCT International Application No. PCT/US2018/015392, filed on Jan. 26, 2018 entitled "GAS SENSOR AND METHODS OF OPTIMIZING AN ARRAY OF GAS SENSORS" which claims priority under 35 U.S.C. § 119(e) from U.S. provisional patent application No. 62/451,090, filed on Jan. 27, 2017, entitled "MULTI-ELEMENT SAW/QCM DEVICES WITH MOFS COMBINED WITH INTELLIGENT ANALYTICS FOR COMPLEX GAS SENSING", the contents of which are incorporated herein by reference.

GOVERNMENT CONTRACT

This invention was made with government support under grant #DE-FE0004000 awarded by the Department of Energy (DOE). The government has certain rights in the invention.

BACKGROUND OF THE INVENTION

1. Field of the Invention

The present invention relates to electronic nose devices, and, more particularly, to an electronic nose device that includes metal-organic frameworks (MOFs) deposited on arrays of surface acoustic wave (SAW) sensors or quartz crystal microbalance (QCM) sensors.

2. Description of the Related Art

The ability to broadly identify the contents of arbitrary gas mixtures (i.e., to smell) is currently not possible with any portable device. The "electronic noses" that currently exist are highly specialized for specific gas mixtures (unlike biological noses), and furthermore can typically only report the concentration of a single gas from the mixture. A true electronic analog of the biological nose would have a very broad range of gas sensing capability, and the availability of such a device would have enormous social benefit. From detecting diseases via a person's odor or breath, to monitoring air quality and detecting dangerous gas leaks, to finding hidden landmines, there are countless uses for electronic noses that today are either unfulfilled, or are accomplished using dog's noses. Notwithstanding the impressive olfactory capabilities of dogs, their widespread use for applications as critical as landmine detection highlights the absence of sufficiently advanced gas sensors that could be used in their place.

The capabilities of traditional electronic nose devices have been limited for two fundamental reasons. First, the sensing materials have been chosen by experimental trial-and-error. All gas sensors employ a sensing material, which binds to the molecules in the gas mixture, and a transduction mechanism that generates a signal whenever that binding occurs. Electronic noses require arrays of dissimilar sensing materials that work cooperatively; each material needs to bind to a different set of gas molecules in order for the device to distinguish between the species in the mixture. Because traditional sensing materials, such as polymer thin films, have been amorphous, it has not been possible to precisely predict the interactions between the gas molecules and the sensing materials, which requires precise knowledge of the material's atomic structure. The inability to make such predictions meant that only experimental trial-and-error could be used to find suitable sets of sensing materials. If finding a single sensing material that can strongly bind a desired gas species is difficult, finding ten or a hundred that work cooperatively is possible but purely empirical, which makes optimization of arrays challenging.

The second limitation of traditional electronic nose devices is that they require training. Training an electronic nose is the process where a device is exposed to a known gas mixture in a controlled environment and its signal response is recorded in a database. This training is then repeated for many different gas mixtures under a variety of temperature and humidity conditions. Then, when the electronic nose is exposed to an unknown gas mixture, the new signal is compared against previously recorded signals to find the closest match. However, it is impossible for an electronic nose to identify a gas species that is not present in the training set. Furthermore, any change in environmental conditions, including shifting properties of the sensor itself, can invalidate the training data (resulting in a phenomenon known as sensor drift). This training process is laborious, and hence the resulting electronic noses tend to be specialized for a narrow range of gas mixtures.

SUMMARY OF THE INVENTION

In accordance with an aspect of the disclosed concept, a gas sensor comprises: at least one sensor device including a surface acoustic wave (SAW) device or a quartz crystal microbalance (QCM) device; and a layer of metal organic framework (MOF) material disposed on each of the at least one sensor device, wherein the at least one sensor device is structured to sense a change in mass of the MOF material.

In accordance with another aspect of the disclosed concept, a method of optimizing an array of gas sensors each including a sensor device having a layer of MOF material disposed thereon, wherein the sensor device is structured to sense a change in mass of the MOF material comprises: selecting a plurality of gas mixtures; selecting a plurality of MOF materials; selecting a plurality of array sizes, the array size being the number of gas sensors in the array; generating a set of potential arrays from the plurality of MOF materials and the plurality of array sizes, each of gas sensors in a selected potential array includes a different type of MOF material; simulating adsorption characteristics of each of the MOF materials for each of the gas mixtures; calculating an effectiveness score for each of the potential arrays; and selecting one or more of the potential arrays based on the calculated effectiveness scores.

BRIEF DESCRIPTION OF THE DRAWINGS

A full understanding of the disclosed concept can be gained from the following description of the preferred embodiments when read in conjunction with the accompanying drawings in which.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components ire "coupled" shall mean that the parts arc joined or operate together either directly or indirectly, i.e., through one or more intermediate parts or components, so long as a link occurs.

As used herein, the term "number" shall mean one or an integer greater than one (i.e., a plurality).

As employed herein, the term "processor" shall mean a programmable analog and/or digital device that can store, retrieve, and process data; a microprocessor; a microcontroller; a microcomputer; a central processing unit; or any suitable processing device or apparatus.

The present invention will now be described, for purposes of explanation, in connection with numerous specific details in order to provide a thorough understanding of the subject invention. It will be evident, however, that the present invention can be practiced without these specific details without departing from the spirit and scope of this innovation.

The disclosed concept provides a fundamentally new kind of electronic nose that is rationally designed, and does not require training. The signal directly conveys chemical composition data without the need for comparing to prior signals in a database. The elimination of training means that a much wider range of gases could be detected, at a greater range of environmental conditions, and sensor drift would be dramatically mitigated.

The disclosed concept uses combinations of metal-organic frameworks (MOFs), which are self-assembled nanoporous crystals with extremely high surface areas. The pores of MOFs can be tuned to different shapes and sizes, in order to maximize their interaction with specific gases. The crystalline nature of MOFs (unlike traditional gas sensing materials which are amorphous) make it possible to accurately predict gas adsorption via molecular simulations, which allows for intelligent sensing analytics.

The MOFs are deposited on arrays of surface acoustic wave (SAW) sensors (or QCM sensors), which transduce the signal of adsorbed gas by measuring the change in mass. The use of MOFs, whose gas adsorption can be accurately simulated, means the whole array can be predictively modeled in silico. This not only eliminates the need for training, it allows the entire device to be computationally optimized to give maximum performance without relying on experimental trial-and-error.

The disclosed concept uses an intelligent analytics algorithm that combines probabilistic estimations of the ambient gas composition from each element of the sensor array, via joint probability distributions, to accurately (and with high precision) provide a read out of the gases in the ambient gas environment.

Figure 1:
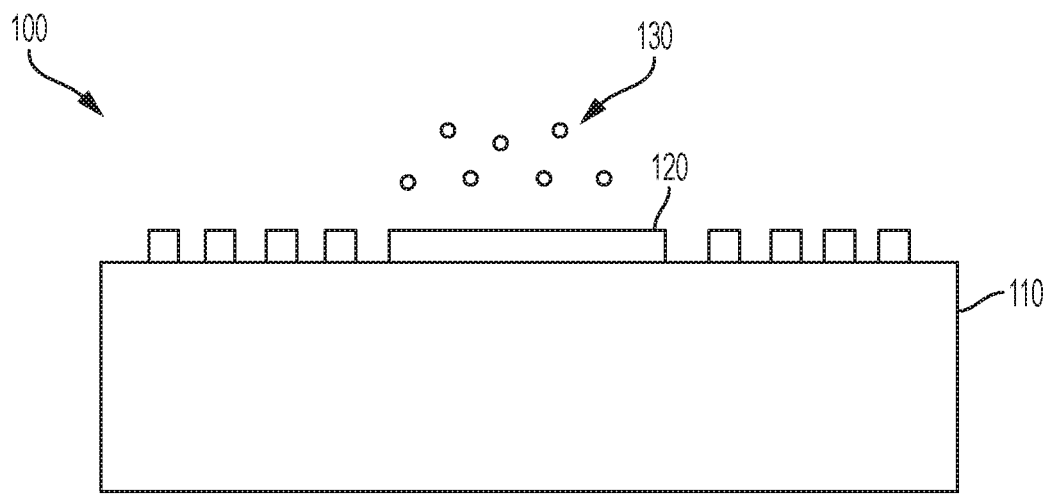
FIG. 1 is a diagram of a gas sensor including a surface acoustic wave (SAW) device and a layer of metal organic framework (MOF) material in accordance with an example embodiment of the disclosed concept.

FIG. 1 is a diagram of a gas sensor 100 in accordance with an example embodiment of the disclosed concept. The gas sensor 100 includes a SAW device 110. A layer of MOF material 120 is disposed on the SAW device 110. The MOF material 120 may be any type of MOF material 120. In some example embodiments of the disclosed concept, the MOF material 120 is selected from ZIF-8, IRMOF-1, HKUST-1, NU-125, UiO-66, NU-100, and MgMOF-75. In some example embodiments, the layer of MOF material 120 is formed from ZIF-8. In some other example embodiments, an array of gas sensors 100 is employed and the individual gas sensors 100 forming the array may employ different types of MOF materials. However, it will be appreciated by those having ordinary skill in the art that any type of MOF material may be employed without departing from the scope of the disclosed concept.

In some example embodiments of the disclosed concept, the layer of MOF material 120 may have a thickness within a range of about 100-300 nm. It has been found that the sensitivity of the SAW device 110 increases with the thickness of the layer of MOF material 120. However, it will be appreciated by those having ordinary skill in the art that other thicknesses of the layer of MOF material 120 may be employed without departing from the scope of the disclosed concept.

In some example embodiments of the disclosed concept, the SAW device 110 may have SAW reflective delay lines with operating frequency of 436 MHz. The SAW reflective delay lines may be fabricated on Y-Z $LiNbO_3$. The layer of MOF material 120 is coated on the SAW reflective delay lines. However, it will be appreciated that other arrangements of SAW devices may be employed without departing from the scope of the disclosed concept.

The MOF material 120 is structured to adsorb a gas mixture 130 and the SAW device 110 is structured to sense a change in the mass of the MOF material 120 due to the adsorption of the gas mixture 130. The MOF material 120 may be selective toward particular gases in the gas mixture 130. For example, the MOF material 120 may be selective toward $CO_2$ and $CH_4$ against other competing gases CO, $H_2$, and air. The MOF material 120 may also have a large sensitivity toward $CO_2$ compared to $CH_4$. The MOF material 120 is stable in ambient condition and can be grown as uniform thin films on various substrates at room temperature.

The change in mass of the MOF material 120 sensed by the SAW device 110 is indicative of the presence of particular gases in the gas mixture 130, and in particular, indicative of the presence of particular gases that the MOF material 120 is selective toward. In some embodiments of the disclosed concept, the SAW device 110 detects the change in mass of the MOF material 120 (e.g., the mass of the gas mixture 130 adsorbed by the MOF material 120) by sensing a change in velocity (frequency or phase) or amplitude of SAWs that propagate along the surface of the SAW device 110. In some example embodiments, sensing the change in velocity is preferred as it remains unaffected from electromagnetic interference. However, it will be appreciated that using a change in amplitude of the SAWs may instead be employed without departing from the scope of the disclosed concept.

An output of the SAW device 110 may be provided via a wired method or a wireless method. For example and without limitation, the output of the SAW device 110 may be wired to a processor or other circuitry and provide its output to the processor or other circuitry. The output of the SAW device 110 is indicative of the change in mass of the MOF material 120 and the processor or other circuitry may use the output of the SAW device 110 to determine components of the gas mixture 130 based on the output of the SAW device 110. The SAW device 110 may also provide its output in a wireless manner. For example, an output of the SAW device 110 may be connected to an antenna and the output of the SAW device 110 may be provided wirelessly to another device via the antenna.

Figure 2:
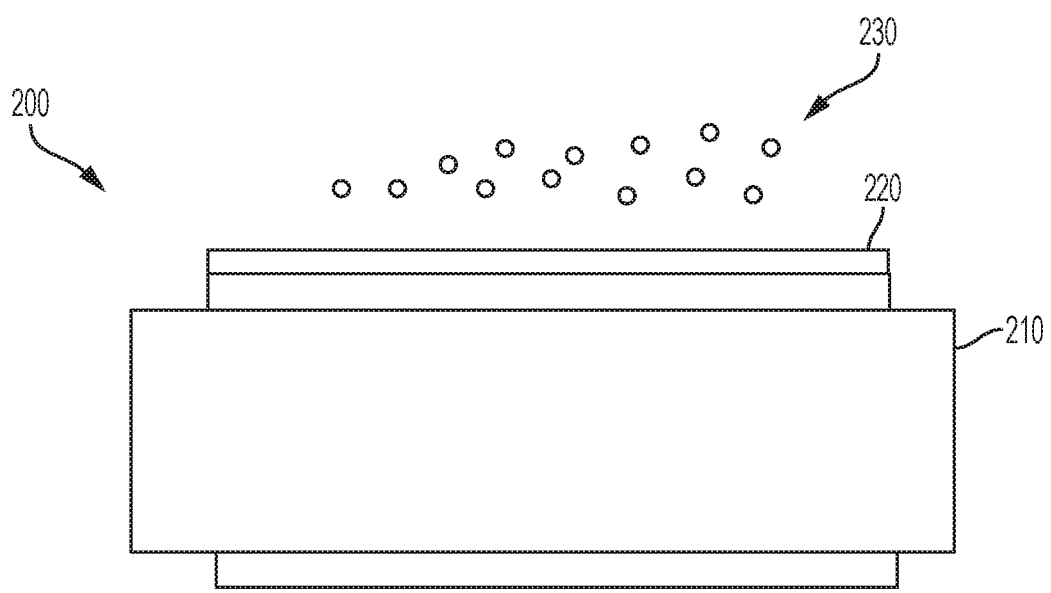
FIG. 2 is a diagram of a gas sensor including quartz crystal microbalance (QCM) device and a MOF material in accordance with an example embodiment of the disclosed concept.

FIG. 2 is a diagram of a gas sensor 200 in accordance with another example embodiment of the disclosed concept. The gas sensor 200 of FIG. 2 includes a QCM device 210. A layer of MOF material 220 is disposed on the QCM device 220. The MOF material 220 is structured to adsorb components of a gas mixture 230 and the QCM device 210 is structured to sense a change in mass of the MOF material 220. Based on the change in mass of the MOF material 220, components of the gas mixture 230 may be determined.

The gas sensor 200 of FIG. 2 operates similar to the gas sensor 100 of FIG. 1. However, the gas sensor 200 of FIG. 2 uses the QCM device 210 to sense a change in mass of the MOF material 220 rather than the SAW device 110. It will be appreciated that the types of MOF material 220 used and their range of thicknesses may be similar to those described with respect to the example embodiment shown in FIG. 1. It will also be appreciated that the QCM device 210 may provide its output in a wireless mode or a wired mode similar to the SAW device 110 described with respect to FIG. 1.

Figure 3:
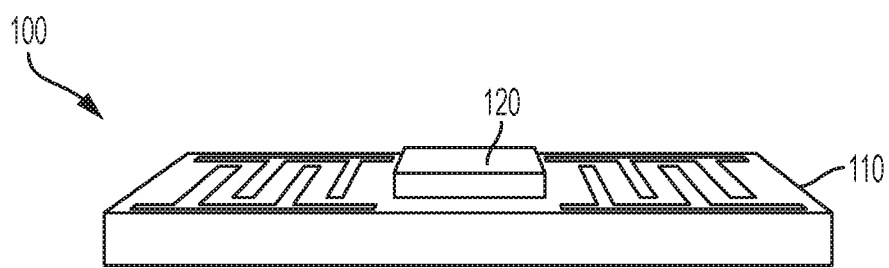
FIG. 3 is a diagram of a gas sensor including a SAW device and a layer of MOF material in accordance with an example embodiment of the disclosed concept.
Figure 4A:
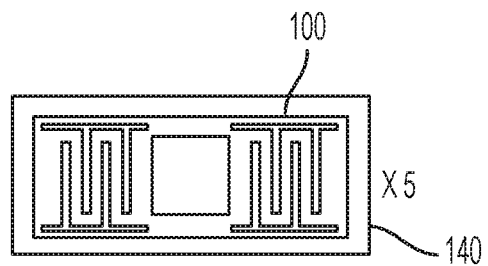
FIGS. 4A-4C are diagrams of examples of gas sensor arrays in accordance with example embodiments of the disclosed concept.
Figure 4B:
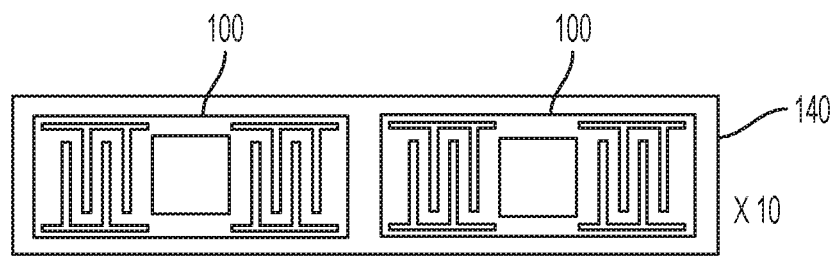
Figure 4C:
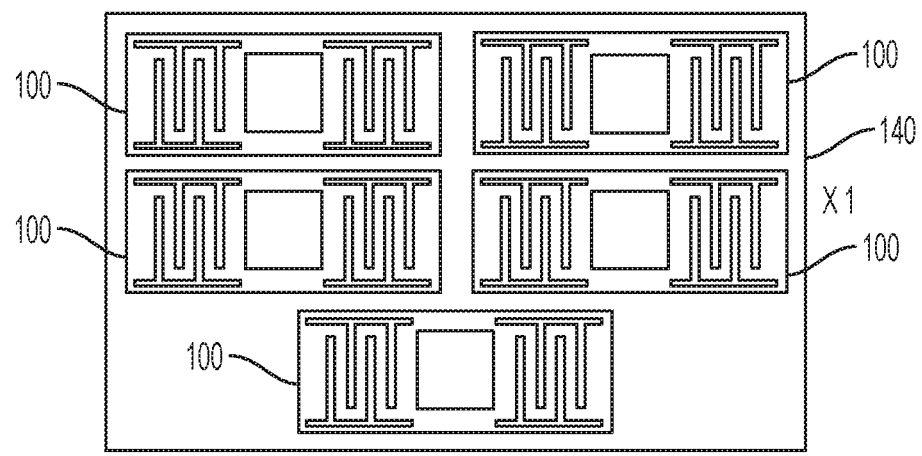

FIG. 3 is another view of the gas sensor 100 including the SAW device 110 and the MOF material 120 according to an example embodiment of the disclosed concept. In some example embodiments, an array of gas sensors 100 is provided. The array of gas sensors may be provided in a variety of manners. FIGS. 4A, 4B, and 4C provide a few examples of arrangements of arrays of gas sensors 100. For example, FIG. 4A illustrates a gas sensor 100 provided on a base 140. Five such bases 140 including one gas sensor 100 are provided in the array of FIG. 4A. FIG. 4B illustrates two gas sensors 100 provided on a base 140. Ten such bases 140 including two gas sensors 100 are provided in the array of FIG. 4B. FIG. 4C illustrates five gas sensors 100 provided on a base 140. One such base 140 is provided in the array of FIG. 4C. While FIGS. 4A, 4B, and 4C provide a few examples of arrays of gas sensors 100, it will be appreciated that any type of array of gas sensors 100 may be employed without departing from the scope of the disclosed concept. It will also be appreciated that each gas sensor 100 in the arrays may employ the same or different MOF materials 120. The number of gas sensors 100 used in the array and the types of MOF materials 120 employed changes in the effectiveness of the array in sensing components in a gas mixture. As will be described herein, methods of optimizing the array of gas sensors 100 may be employed to determine an optimally effective array of gas sensors 100.

Figure 5A:
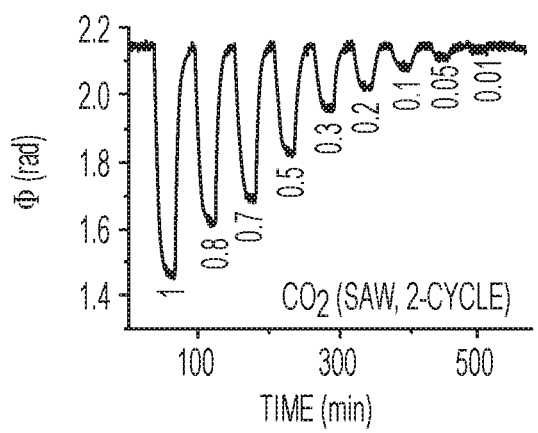
FIGS. 5A-5D are plots of test results using a gas sensor including a SAW deuce and a layer of MOF material.
Figure 5B:
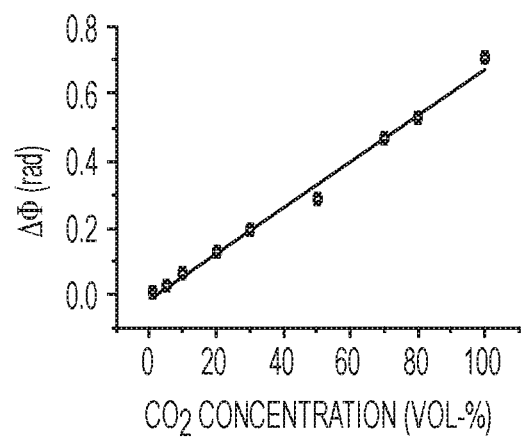

FIGS. 5A-5D are plots of test results using a gas sensor 100 including a SAW device 110, such as that illustrated in FIG. 1, with a layer of ZIF-8 MOF material 120 having a thickness of 200 nm. In FIGS. 5A and 5B, the gas mixture 130 was controlled over time to have different concentrations of $CO_2$ (100%, 80%, 70%, 50%, 30%, 20%, 10%, 5%, and 1%). FIG. 5A illustrates the change in phase sensed by the SAW device 110 (i.e., the change in mass of the MOF material 120) over this period of time. As shown in FIG. 5A, the gas sensor 100 is able to sense the changes in concentration of $CO_2$ in the gas mixture 130. FIG. 5B is a plot that shows the change in phase sensed by the SAW device 110 against the concentration of $CO_2$ in the gas mixture 130. The plot in FIG. 5B shows a liner relationship between the change in phase sensed by the SAW device 110 and the concentration of $CO_2$ in the gas mixture 130. In the example shown in FIGS. 5A and 5B, it was determined that the phase sensed by the SAW device 110 changes by 0.394 degrees per percent change in the concentration of $CO_2$ in the gas mixture 130.

Figure 5C:
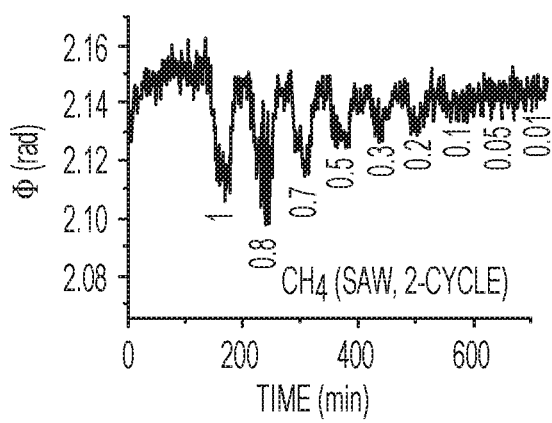
Figure 5D:
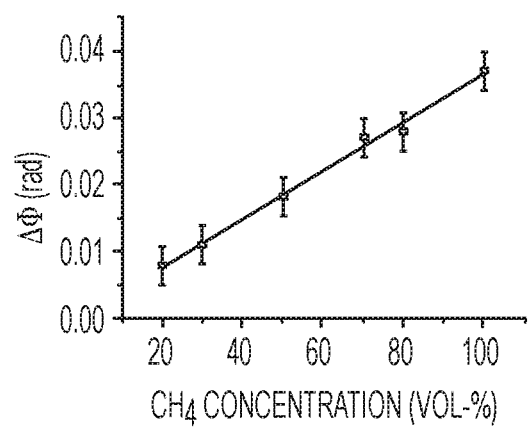

FIGS. 5C and 5D are similar to FIGS. 5A and 5B, except that the concentration of $CH_4$, rather than $CO_2$, in the gas mixture was varied. In the example shown in FIGS. 5C and 5D, it was determined that the phase sensed by the SAW device 110 changes by 0.021 degrees per percent change in the concentration of $CO_2$ in the gas mixture 130.

Figure 6A:
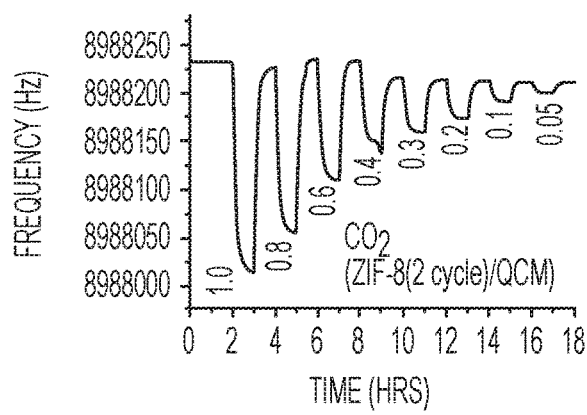
FIGS. 6A-6D are plots of test results using a gas sensor including a QCM device and a layer of MOF material.
Figure 6B:
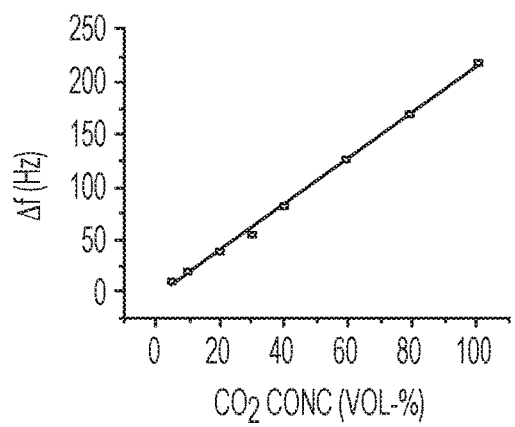

FIGS. 6A-6D are plots of test results using a gas sensor 200 including a QCM device 210, such as that illustrated in FIG. 2, with a layer of ZIF-8 MOF material 220 having a thickness of 200 nm. In FIGS. 6A and 6B, the gas mixture 230 was controlled over time to have different concentrations of $CO_2$ (100%, 80%, 70%, 50%, 30%, 20%, 10%, 5%, and 1%). FIG. 6A illustrates the change in frequency sensed by the QCM device 210 (i.e., the change in mass of the MOF material 220) over this period of time. As shown in FIG. 6A, the gas sensor 200 is able to sense the changes in concentration of $CO_2$ in the gas mixture 230. FIG. 6B is a plot that shows the change in frequency sensed by the QCM device 210 against the concentration of $CO_2$ in the gas mixture 230. The plot in FIG. 6B shows a liner relationship between the change in frequency sensed by the QCM device 210 and the concentration of $CO_2$ in the gas mixture 230. In the example shown in FIGS. 6A and 6B, it was determined that the frequency sensed by the QCM device 210 changes by 2.18 Hz per percent change in the concentration of $CO_2$ in the gas mixture 230.

Figure 6C:
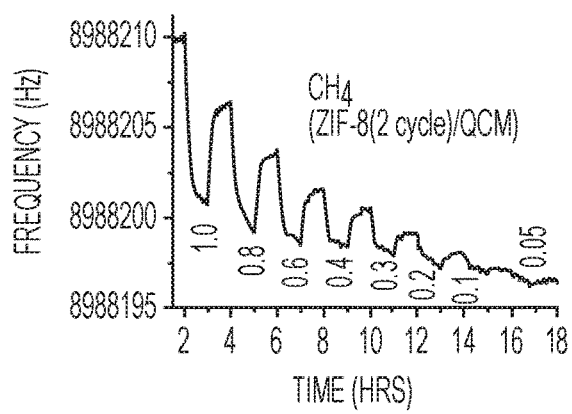
Figure 6D:
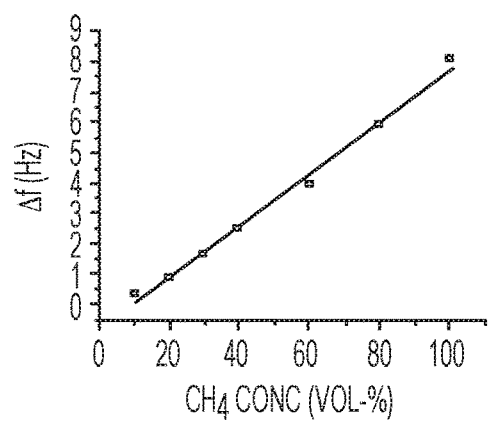

FIGS. 6C and 6D are similar to FIGS. 6A and 6B, except that the concentration of $CH_4$, rather than $CO_2$, in the gas mixture was varied. In the example shown in FIGS. 6C and 6D, it was determined that the frequency sensed by the QCM device 210 changes by 0.09 Hz per percent change in the concentration of $CO_2$ in the gas mixture 230.

Figure 7A:
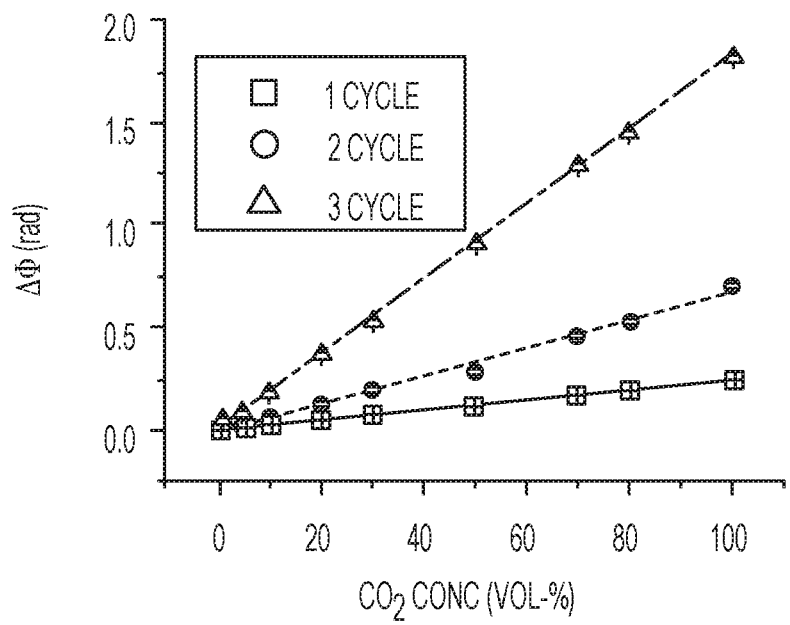
FIGS. 7A and 7B are plots showing the effectiveness of changing the thickness of the MOF material in a gas sensor.
Figure 7B:
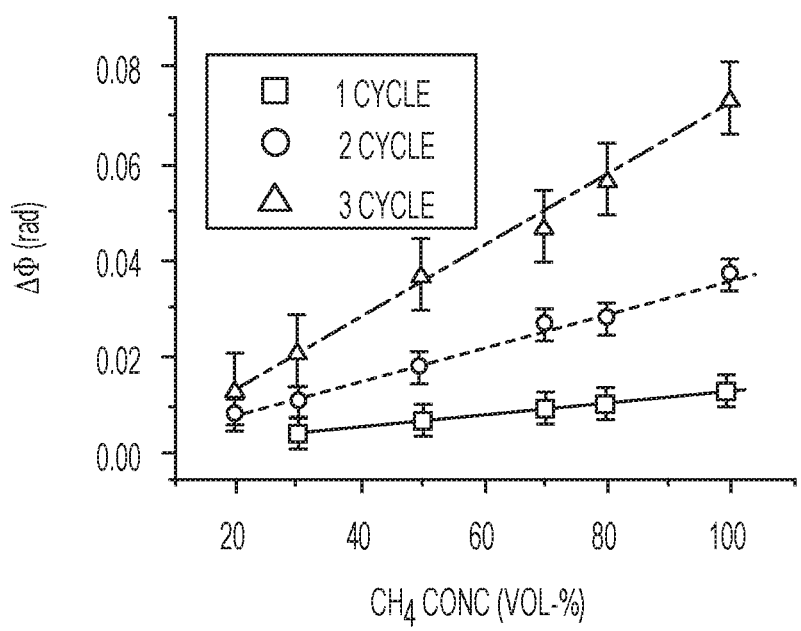

FIGS. 7A and 7B are plots showing the effectiveness of changing the thickness of the MOF material 120 in the gas sensor 100 including the SAW device 110 from the example embodiment of FIG. 1. FIG. 7A shows the change in phase sensed by the SAW device 110 against the concentration of $CO_2$ in the gas mixture 130 for thicknesses of 100 nm (1-cycle), 200 nm (2-cycle), and 300 nm (3-cycle). FIG. 7B shows the change in phase sensed by the SAW device 110 against the concentration of $CH_4$ in the gas mixture 130 for thicknesses of 100 nm (1-cycle), 200 nm (2-cycle), and 300 nm (3-cycle). As shown in FIGS. 7A and 7B, the sensitivity of the gas sensor 100 increases as the thickness of the layer of MOF material 120 increases over at least a range of thicknesses.

Figure 8:
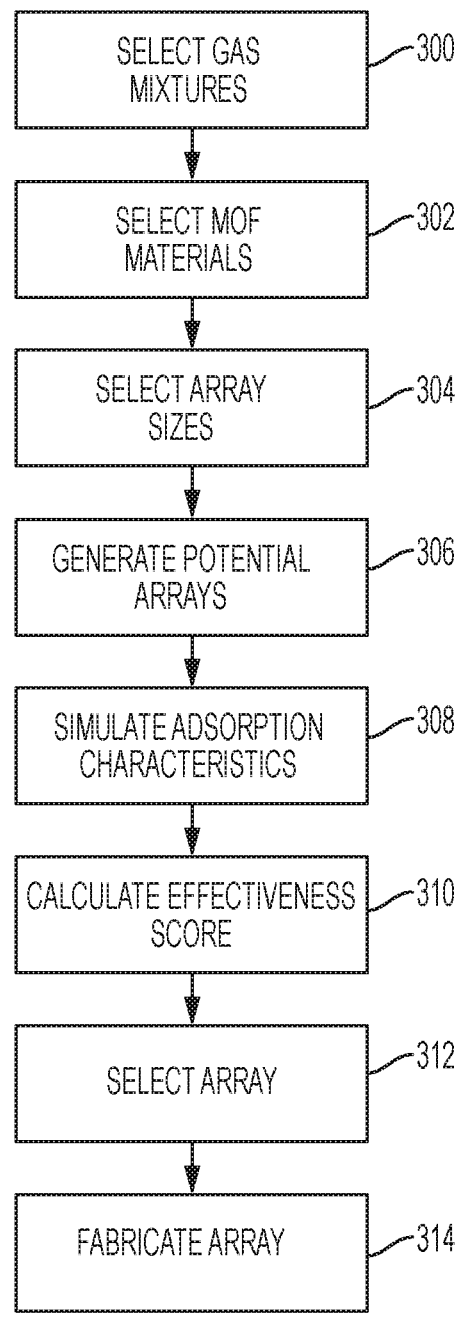
FIG. 8 is a flowchart of a method of optimizing an array of gas sensors in accordance with an example embodiment of the disclosed concept.

FIG. 8 is a flowchart of a method of optimizing an array of gas sensors in accordance with an example embodiment of the disclosed concept. The method may be employed to select an optimal array of gas sensors formed from gas sensors such as the gas sensor 100 including a SAW device 110 and a MOF material 120 shown in FIG. 1. It will also be appreciated that the method may be used to select an optimal array of gas sensors formed from the gas sensor 200 of FIG. 2 or other gas sensors using MOF materials.

The method begins at 300 where a plurality of gas mixtures are selected. The gas mixtures may have gas components of interest such as $CH_4$, $N_2$, $O_2$, $CO_2$, $C_2H_6$, any combination or subset thereof, or any other gas components. The set of gas mixtures may be formed by varying the concentrations of each of the gas components in selected ranges of mole fractions. In some example embodiments of the disclosed concept, the gas components are varied in concentration by a predetermined step size (e.g., without limitation, 1%) in a range of mole fractions from 0-1 to generate the set of gas mixtures.

Next, at 302, a plurality of MOF materials are selected. In some example embodiments of the disclosed concept, the MOF materials are selected from IRMOF-1, HKUST-1, NU-125, UiO-66, ZIF-8, MgMOF-74, NU-100, MOF-177, and MOF-801. However, it will be appreciated that any type of MOF material may be used in the selected set of MOF materials. At 304, a plurality of array sizes are selected. The array size is the number of gas sensors that will be used in an array.

At 306, potential arrays are generated. The potential arrays are generated from the selected array sizes and MOF materials. Each gas sensor in a potential array uses a different MOF material. For example, if the selected array sizes are 1 and 2 and the selected MOF materials are ZIF-8 and UiO-66, the potential arrays will include an array using a single gas sensor with ZIF-8, an array using a single gas sensor with UiO-66, and an array including two gas sensors, one using ZIF-8 and one using UiO-66. It will be appreciated that larger array sizes and more MOF materials may be selected without departing from the scope of the disclosed concept. It will also be appreciated that a targeted set of potential arrays may be selected directly rather than being generated from the selected array sizes and MOF materials.

At 308, the adsorption characteristics of each of the selected MOF materials for each of the selected gas mixtures is simulated. In some example embodiments, grand canonical Monte Carlo (GCMC) simulations are performed for each of the MOF materials. In an example embodiment, the simulations determine the adsorption data for the selected MOF materials at 298K and 1 bar. The adsorption data is the change in mass of the MOF material due to adsorption when exposed to the gas mixture.

At 310, an effectiveness score of each potential array is calculated. The effectiveness score is a representation of the effectiveness of the potential array in sensing the composition of the gas mixture. At 312, a potential array is selected based on the calculated effectiveness scores and at 314 the selected potential array is fabricated.

In accordance with an example embodiment of the disclosed concept, the effectiveness score is calculated by calculating a sensor array gas space (SAGS) score for each potential array.

The SAGS score has the property that it is high for arrays that have very distinct mass responses between gas mixtures that are similar in composition, and low for arrays that have similar mass responses when the gas compositions are very different. To calculate an array's SAGS score, first we calculate a pairwise array score, $S_{ij}$, as shown in Equation 1, $$S_{ij} = \frac{m_{ij}}{d_{ij}}, \tag{1}$$

where $d_{ij}$ is the Euclidean distance between two different gas compositions, i and j, each with N component gases, specified by their mole fraction, $x_k$, as shown in Equation 2, $$d_{ij} = \sqrt{\sum_{k=1}^{N} (x_{k,i} - x_{k,j})^2}, \tag{2}$$

and $m_{ij}$ is the Euclidean distance between the mass changes in an M element MOF array adsorbing either gas mixture i or gas mixture j, as shown in Equation 3.

$$m_{ij} = \sqrt{\sum_{k=1}^{M} (m_{k,i} - m_{k,j})^2}, \tag{3}$$

The pairwise array score indicates how well a MOF array can distinguish between a pair of gas mixtures. To calculate the SAGS score, the pairwise array score is calculated over all pairs of gas mixtures in a given space of gas mixtures, and then the average is taken, as shown in Equation 4, $$\phi_W = \frac{\Sigma S_{ij}}{W}, \tag{4}$$

where W is the total number of combinations of pairs of gas mixtures used in the average. For example, 78 gas mixtures will result in 3003 pairs of gas mixtures.

A high SAGS score ($\phi_W$) means that, over the range of gas compositions considered, the array is good at distinguishing between very similar mixtures. Each combination of MOF materials in the array has its own SAGS score for a particular choice of gas mixtures. In some example embodiments of the disclosed concept, the SAGS score may be used as the effectiveness score and the potential array having the highest SAGS score may be selected to be fabricated.

It will also be appreciated that in some example embodiments, the highest effectiveness scores may be used as a consideration in selecting the array to be fabricated, but the array with the highest effectiveness score may not necessarily be selected. For example, increasing the array size may only marginally improve the effectiveness score. The cost considerations in creating a larger array for only a marginal improvement may lead to selecting an array having a smaller array size to be fabricated. However, the effectiveness score itself is informative in indicating which specific MOF materials and combination of MOF materials are effective in distinguishing between gas mixtures and the selection of the optimal array to fabricate can be based on the effectiveness score in combination with other considerations such as cost.

Figure 9:
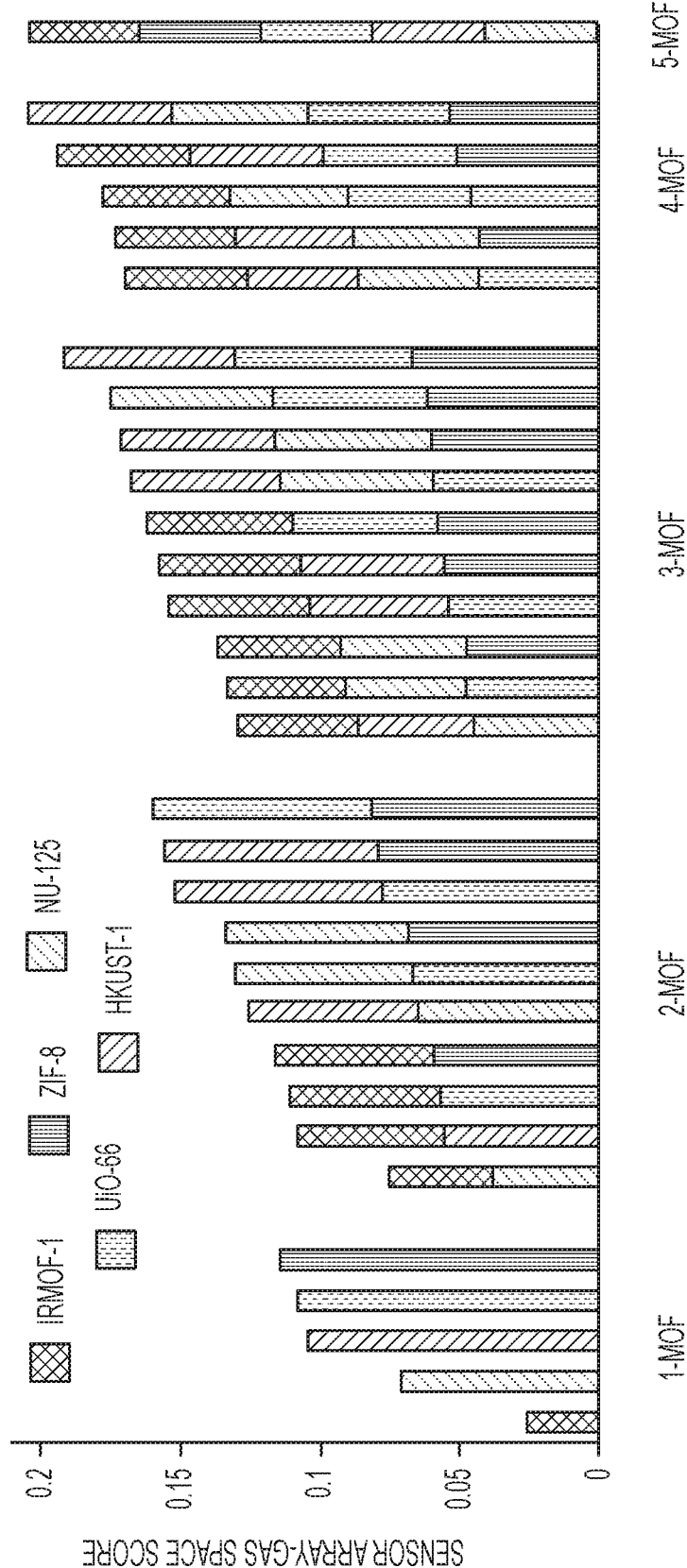
FIG. 9 is a plot showing the calculated sensor array gas space (SAGS) scores for arrays of varying an sizes and MOF materials in accordance with an example embodiment of the disclosed concept.

FIG. 9 is a plot showing the calculated SAGS scores for arrays of varying array sizes and MOF materials. As shown in FIG. 9, arrays having a larger array size typically have a higher SAGS score. While there is a large difference in the score between the best and worst MOF among the 1-MOF arrays, the gaps between the best and worst arrays of larger sizes are relatively smaller. Notably, this is because the worst 1-MOF sensors become significantly better when other MOFs are added to them. Whereas a single MOF can have a very low score (e.g., IRMOF-1: 0.025), the score of the worst pair was more than double (IRMOF-1 and NU-125: 0.075). Therefore, when designing new MOFs for gas sensing application, it may be easier to find two that work well together than to find one with high performance.

As shown in FIG. 9, the best scoring three-MOF array consists of HKUST-1, UiO-66, and ZIF-8 and has a SAGS score of 0.192 while the five-MOF array consisting of HKUST-1, NU-125, UiO-66, IRMOF-1, and ZIF-8 has a SAGS score of 0.205. Based on the results, even though the five-MOF array has the highest SAGS score, the marginal improvement over the three-MOF array may not warrant the extra cost and the three-MOF array may be selected to be fabricated.

Calculating the SAGS score under different conditions can reveal the effectiveness of different arrays of MOF materials under specific circumstances. For example, changing the pressure from 1 bar to 10 bar results in different SAGS scores and an array that was optimal at 1 bar may not be optimal at 10 bar. Additionally, comparing the SAGS scores of different arrays can be used to quantify characteristics such as the effectiveness of adding a certain MOF material to an array.

Figure 10:
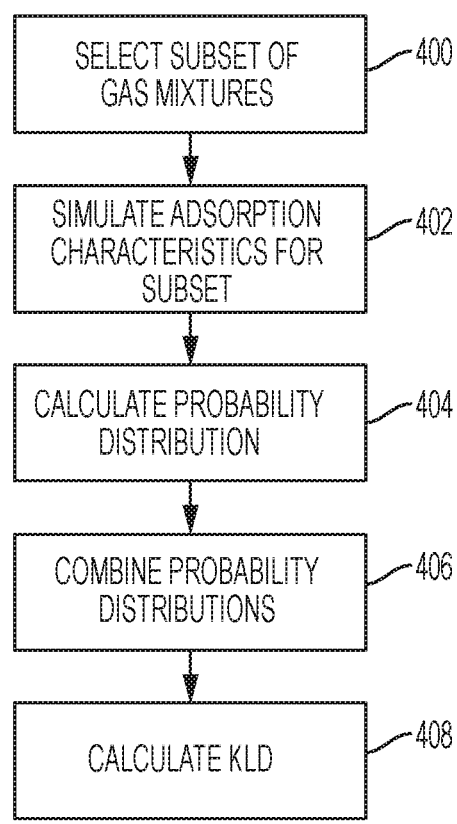
FIG. 10 is a flowchart of a method of calculating a Kullback-Liebler divergence (KLD) in accordance with an example embodiment of the disclosed concept.

In another example embodiment of the disclosed concept, a Kullback-Liebler divergence (KLD) is used as the effectiveness score. FIG. 10 is a flowchart of a method of calculating the KLD as the effectiveness score. The method shown in FIG. 10 may be used as step 310 in the method of FIG. 8.

For the method of FIG. 10, the plurality of gas mixtures selected in step 300 of the method of FIG. 8 are selected by selecting a plurality of gas components and varying each of the gas components in concentrations from 0-1 mole fractions in a predetermined step size (e.g., without limitation, 1%) to generate the plurality of gas mixtures. In some example embodiments, concentrations of the gas components $CH_4$, $N_2$, and $O_2$ are varied in steps of 1% resulting in a total of 5,151 gas mixtures.

At 400, a subset of the gas mixtures are selected. The subset may include gas mixtures that are of particular interest for an application. However, it will be appreciated that any subset of the gas mixtures may be selected. At 402, the adsorption characteristics for the selected MOF materials are simulated.

At 404, for each of the MOF materials and each of the subset of the plurality of gas mixtures, a probability distribution of the gas mixture from the subset of the plurality of gas mixtures being selected gas mixtures from the plurality of gas mixtures in calculated. In more detail, for each gas mixture in the subset of gas mixtures, the corresponding entry in the previously simulated adsorption characteristics of MOF materials for all of the gas mixtures is removed. The adsorption characteristics of the MOF materials for the selected gas mixture in the subset should be similar to gas mixtures having similar gas compositions. However, the MOF material may have similar adsorption characteristics for multiple gas mixtures. A probability distribution is created indicating the probability that the selected gas mixture from the subset is a particular gas mixture based on the similarity of the adsorption characteristics for the selected gas mixture from the subset to adsorption characteristics of the complete set of gas mixtures for the MOF material.

At 406, the probability distributions of MOF materials are combined to emulate the probability distribution of potential arrays. For example, if a potential array includes three MOF materials, the probability distributions of the three MOF materials are combined to obtain the probability distribution of the potential array. The joint probability is calculated by multiplying discrete probability distributions of each MOF material and then renormalizing so that all of the points add up to one.

At 408, the KLD for each potential array is calculated. The KLD for each potential array is calculated, as shown in Equation 5, $$KLD = \sum_i^N P_i \log \frac{P_i}{Q_i} \quad (5)$$

where a probability at each mole fraction is represented by $P_i$, and a reference probability of $Q_i$ is a probability equivalent to 1/N, where N is the predetermined step size divided by 1.

The KLD value determines the information content of a probability distribution produced by an array, where a higher value is better. Arrays can then be ranked by their KLD values for the various gas mixtures in the subset. When multiple gas mixtures are included in the In one example embodiment, the subset of gas mixtures includes the gas mixtures shown in Table 1.

TABLE 1

| | Component Mole Fraction | |
|---|---|---|
| Experiment # | $CH_4$ | $N_2$ |
| 1 | 0.1 | 0.9 |
| 2 | 0.25 | 0.75 |
| 3 | 0.5 | 0.5 |
| 4 | 0.75 | 0.25 |

Figure 11:
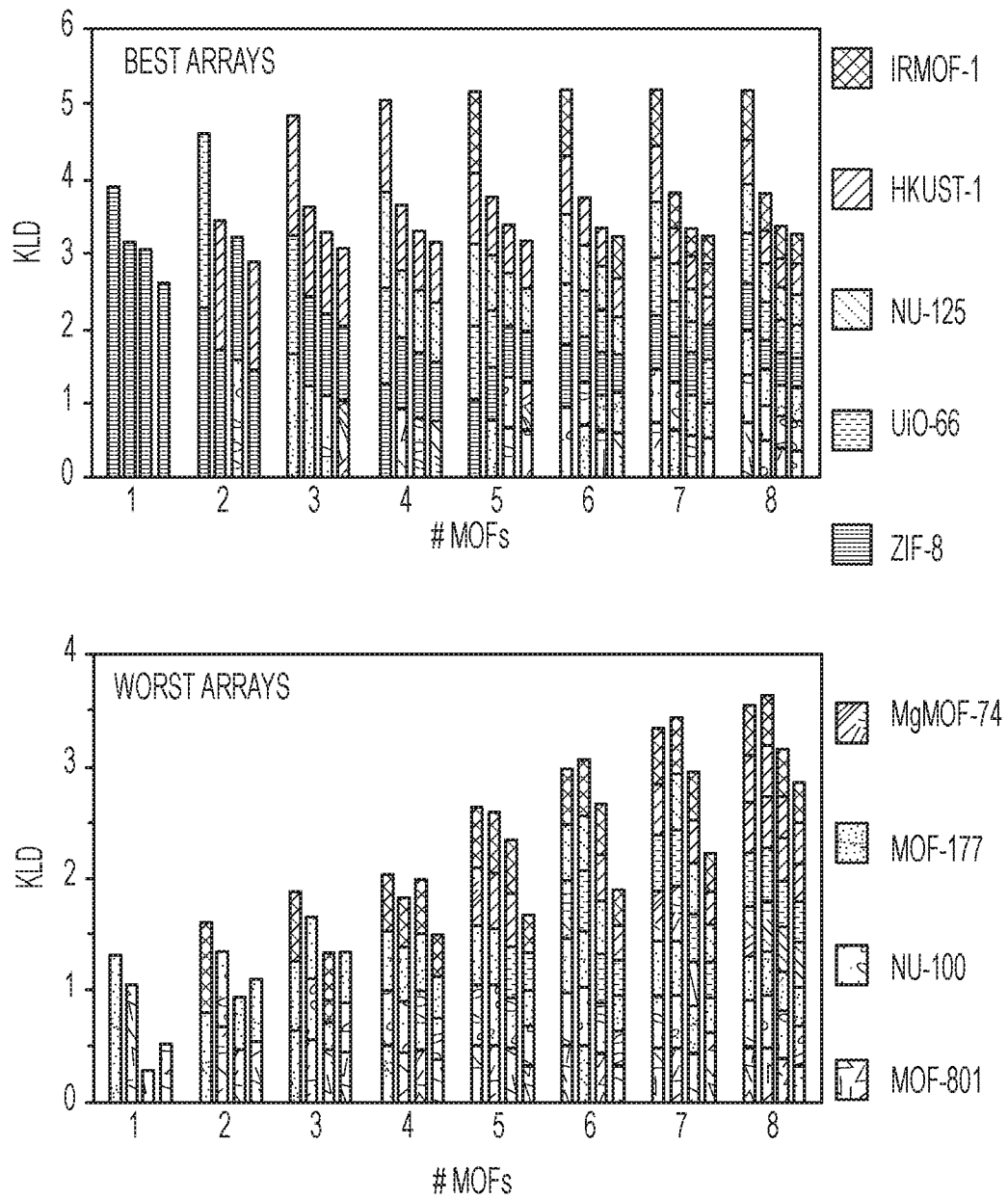
FIG. 11 is a plot showing the calculated KU) for arrays of varying array sizes and MO E materials in accordance with an example embodiment of the disclosed concept.

For array sizes ranging from 1-9 and for the MOF materials IRMOF-1, HKUST-1, NU-125, UiO-66, ZIF-8, MgMOF-74, MOF-177, NU-100, and MOF-801, the average KLD scores for the four gas mixtures shown in Table 1 was calculated. FIG. 11 shows plots of the KLD scores for the best arrays and the worst arrays for the subset of gas mixtures shown in Table 1. In FIG. 11, a group of 4 KLD values is shown for each array size, with the group of KLD values beginning with the gas mixture from experiment one being the leftmost of the group and continuing sequentially to the gas mixture in experiment 4 being the rightmost of the group.

As shown in FIG. 11, the overall KLD increases as array size increases, although more dramatically for the worst arrays. Although MOF configurations differ among experiments with the same array size, particular MOFs stand out as performing consistently well or poor. Moreover, the best one MOF arrays all contain ZIF-8, and in all but one case, the worst MOF is MOF-801. Overall, the best performing MOFs are ZIF-8, HKUST-1, UiO-66, and NU-125 across all array sizes. Conversely, the worst arrays contain MOF-801, NU-100, and MOF-177, and IRMOF-1.

Figure 12:
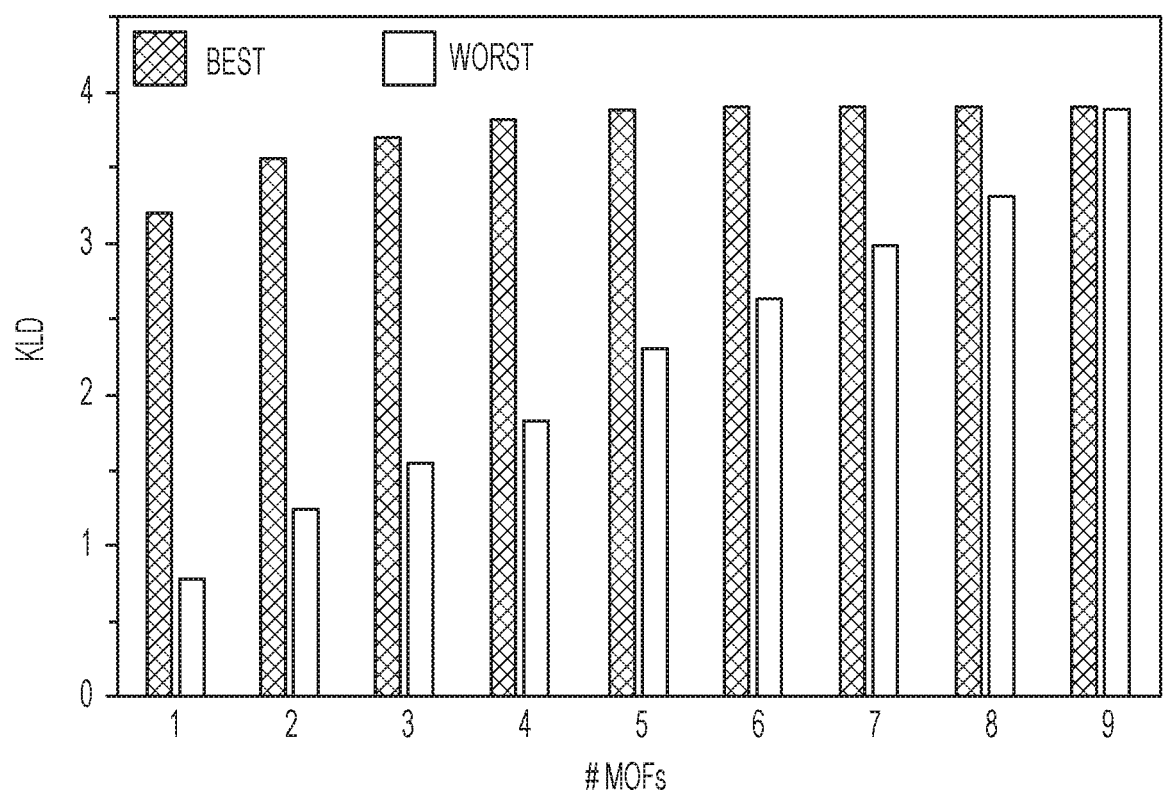
FIG. 12 is a plot showing the calculated average KLD for arrays of varying array sizes and MOF materials in accordance with an example embodiment of the disclosed concept.

As shown in FIG. 11, arrays that perform well (i.e., have high KLD values) for one experimental gas mixture will not necessarily be the best for other gas mixtures. To find arrays that would perform well over the whole $CH_4/N_2$ composition range, the average of the KLDs over all experiments in Table 1 can be taken. FIG. 12 shows a plot of the average KLDs over all the experiments in Table 1. Assessing the trends in array size by averaging the values allows generalization of a "good" vs "bad" KLD value for binary $CH_4/N_2$ mixtures. In the case of the best arrays, the KLD values are relatively high at just one MOF, at 3.20, and peak at an array of five MOFs, at 3.88. On the other hand, the worst arrays start off at a very low KLD value, of 0.79, and show a steady increase as the MOF array size increases, leading up to 3.88 for nine MOFs.

As shown in FIG. 12, the best array for 4 MOF materials performs much better than the worst, at KLDs of 3.81 and 1.84, respectively. This disparity in KLD values highlights the benefits of computational array-design for gas sensing. From 9 possible MOF materials, there are 126 possible configurations of 4-MOF arrays. Thus, it is unlikely that the best array would be selected through a trial-and-error process, where synthesis and testing is time consuming; computational screening can significant expedite the selection process.

A higher KLD value is indicative of the probability that a potential array will correctly predict the concentration value of components of a gas mixture. For example, choosing an optimal 4-MOF array may perform nearly as well as an 8-MOF array, and, when taking into consideration the time and resources to construct larger arrays, the 4-MOF array may be preferable for a particular application.

In the subset of gas mixtures shown in Table 1, a binary mixture of two gas components was used. However, it will be appreciated that the KLD values for potential arrays may be calculated for gas mixtures including more than two gas components. For example, KLD values may be calculated for ternary mixtures of $CH_4$, $N_2$, and $O_2$, or any other mixture of gases.

In some example embodiments of the disclosed concept, the KLD may be calculated for a specific gas component (e.g., $CH_4$) or it may be calculated based on all components (e.g., $CH_4$, $N_2$, and $O_2$). By calculating the KLD based on a single component, a potential array may be selected that is optimal for detecting that component. By calculating the KLD based on all components, a potential array may be selected that maximizes sensitivity to all components. For example, in one experiment, it was determined that a 5 MOF array which best predicts $CH_4$ is: IRMOF-1, HKUST-1, UiO-66, ZIF-8, and MgMOF-75 and for $O_2$ is: IRMOF-1, HKUST-1, MgMOF-74, MOF-177, and NU-100. In some example embodiments, the 5 MOF array that best predicts $CH_4$ may be selected and fabricated for an application where sensitivity to $CH_4$ is important. In this manner, the potential array can be tuned to specifically address the needs of a particular application, whether it is important to be sensitive to a particular component or whether it is important to be sensitive to all components. While increasing the size of the array may result in an improved KLD score, the cost of increasing the size of the array for marginal improvement may be taken into consideration in selecting the optimal array.

As the methods of optimization described herein can be simulated without experimentation, it is possible to determine the effectiveness of multiple different arrays without needing to fabricate and test each of the variations. With just a 4-element MOF array with 9 MOF materials to choose from, there are 126 different possible configurations. Fabricating and testing the performance of the 126 different possible configurations would be prohibitively expensive. Optimizing the array through simulation avoids the cost of fabricating and testing each of the configurations. The effectiveness of the arrays with respect to individual gas components or multiple gas components may be determined as well. Using the methods of optimization described herein, arrays of gas sensors may be optimized through simulation and the optimal array for an application may be selected for fabrication.

Figure 13:
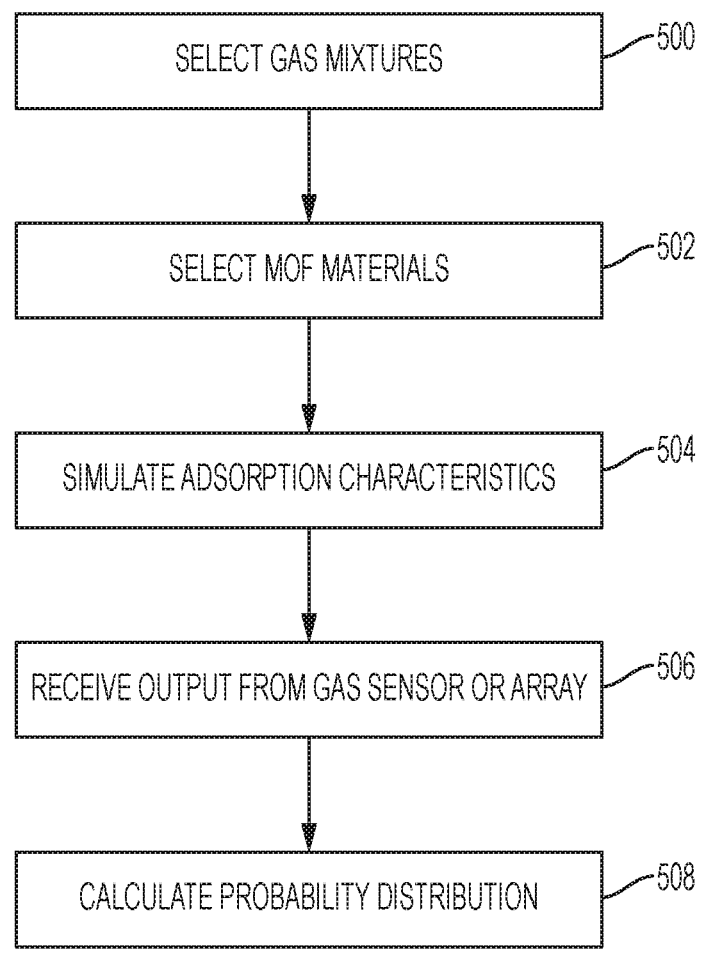
FIG. 13 is a flowchart of a method of converting an output of a gas sensor or an array of gas sensors in accordance with an example embodiment of the disclosed concept.

FIG. 13 is a flowchart of a method of converting an output of a gas sensor or an array of gas sensors in accordance with an example embodiment of the disclosed concept. At 500, a set of gas mixtures is selected similar to step 300 in FIG. 8. For example, the plurality of gas mixtures selected are selected by selecting a plurality of gas components and varying each of the gas components in concentrations from 0-1 mole fractions in a predetermined step size (e.g., without limitation, 1%) to generate the plurality of gas mixtures. In some example embodiments, concentrations of the gas components $CH_4$, $N_2$, and $O_2$ are varied in steps of 1% resulting in a total of 5,151 gas mixtures. At 502, a set of MOF materials are selected similar to step 302 in FIG. 8. At 504, the adsorption of each of the selected MOF materials for each of the selected gas mixtures is simulated. In some example embodiments, GCMC simulations are performed for each of the MOF materials. In an example embodiment, the simulations determine the adsorption data for the selected MOF materials at 298K and 1 bar. The adsorption data is the change in mass of the MOF material due to adsorption when exposed to the gas mixture.

At 506, an output of a gas sensor, such as the gas sensors 100,200 of FIGS. 1 and 2, or an array of gas sensors is received. As it is unknown what the output of the gas sensor means, it is useful to convert the output of the gas sensor into meaningful information. At 508, based on the simulated adsorption characteristics, a probability distribution is created from the output of the gas sensor. The probability distribution indicates the probability that the output of the gas sensor corresponds to each of the selected gas mixtures. By converting the output of the gas sensor to a probability distribution, the probability distribution can be used to predict which gas mixture the gas sensor has sensed. Additionally, it is not necessary to train the gas sensor through experimentation to correspond the output of the gas sensor with different gas mixtures.

Figure 14:
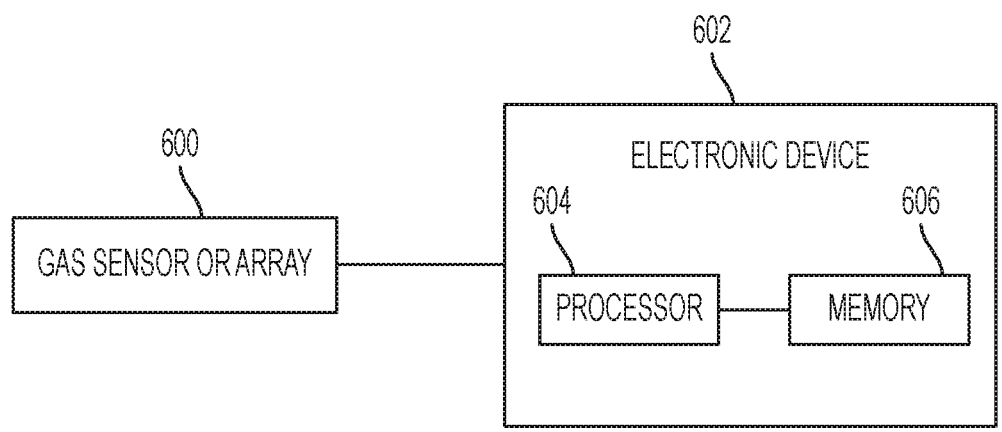
FIGS. 14 and 15 are diagrams of a system including a gas sensor and an electronic device in accordance with example embodiments of the disclosed concept.
Figure 15:
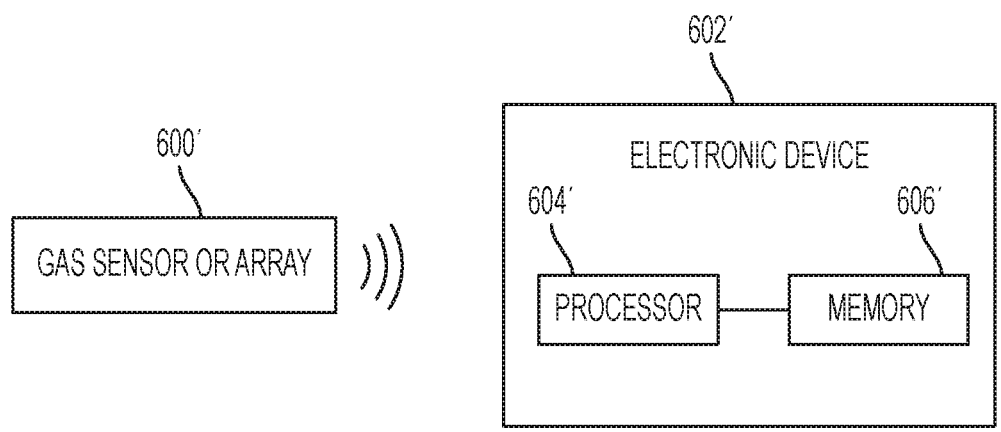

FIGS. 14 and 15 are diagrams of systems including a gas sensor or array 600,600' and an electronic device 602,602'. The gas sensor or array 600,600' may be any type of SAW or QCM gas sensor. The electronic device 602,602' may be a computer, tablet, smartphone, or any other suitable type of electronic device. The electronic device 602,602' is configured to receive the output of the gas sensor or array 600,600' either in a wired manner (FIG. 14) or a wireless manner (FIG. 15). The electronic device 602,602' includes a processor 604,604' and a memory 606,606'.

The memory 606,606' may be included in the processor 604,604' or as a separate component. The processor 604,604' may be, for example and without limitation, a microprocessor, a microcontroller, or some other suitable processing device or circuitry, that interfaces with the memory 606,606' or another suitable memory. The memory 606,606' may be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory 606,606' may also store one or more routines that the processor 604,604' is structured to execute to implement its functions. For example and without limitation, the processor 604,604' may implement some or all of the methods of FIGS. 8, 10, and 13. However, it will be appreciated that some or all of the methods may be implemented in other manners or with other devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas sensor comprising:
   at least one sensor device including a surface acoustic wave (SAW) device; and
   a layer of metal organic framework (MOF) material disposed on each of the at least one sensor device,
   wherein the at least one sensor device is structured to sense a change in mass of the MOF material,
   wherein the at least one sensor device is a plurality of sensor devices arranged in an array, and
   wherein the plurality of sensor devices includes a first sensor device having a first layer of MOF material disposed thereon and a second sensor device having a second layer of MOF material disposed thereon, wherein the first MOF material and the second MOF material are different.

2. The gas sensor of claim 1, wherein the metal organic framework includes at least one of IRMOF-1, HKUST-1, NU-125, UiO-66, and ZIF-8.

3. The gas sensor of claim 1, wherein the sensor device includes the SAW device, and wherein the layer of MOF material has a thickness within a range of about 100-300 nm.

4. The gas sensor of claim 1, wherein the sensor device incudes the QCM device (210), and wherein the layer of MOF material (220) has a thickness within a range of about 100-300 nm.

5. The gas sensor of claim 1, wherein the first layer of MOF material is composed of HKUST-1 and the second layer of MOF material is composed of UiO-66, and wherein the plurality of sensor devices includes a third sensor device having a third layer of material composed of ZIF-8.

6. The gas sensor of claim 1, wherein the first layer of MOF material is composed of IRMOF-1, the second layer of MOF material is composed of HKUST-1, and wherein the plurality of sensor devices includes a third sensor device having a third layer of MOF material composed of UiO-66, a fourth sensor device having a fourth layer of MOF material composed of ZIF-8, and a fifth sensor device having a fifth layer of MOF material composed on MgMOF-74.

7. A method of optimizing an array of gas sensors each including a sensor device having a layer of MOF material disposed thereon, wherein the sensor device is structured to sense a change in mass of the MOF material, the method comprising:
   selecting a plurality of gas mixtures;
   selecting a plurality of MOF materials;
   selecting a plurality of array sizes, the array size being the number of gas sensors in the array;
   generating a set of potential arrays from the plurality of MOF materials and the plurality of array sizes, wherein each of the gas sensors in a selected potential array includes a different type of MOF material;
   simulating adsorption characteristics of each of the MOF materials for each of the gas mixtures;
   calculating an effectiveness score for each of the potential arrays; and
   selecting one or more of the potential arrays based on the calculated effectiveness scores.

8. The method of claim 7, wherein calculating the effectiveness score for each of the potential arrays comprises:
   calculating a sensor array gas space (SAGS) score $\Phi$ for each of the potential arrays based on the following equation:

$$\phi_W = \frac{\Sigma S_{ij}}{W}$$

where W is a total number of combinations of pairs of gas mixtures selected from the plurality of gas mixtures and where $S_{ij}$ is a pairwise array score based on the following equation:

$$S_{ij} = \frac{m_{ij}}{d_{ij}}$$

where $d_{ij}$ is the Euclidean distance between two different gas mixtures, i and j, selected from the plurality of gas mixtures, each with N component gases, specified by their mole fraction, $x_k$, based on the following equation:

$$d_{ij} = \sqrt{\sum_{k=1}^{N} (x_{k,i} - x_{k,j})^2}$$

and $m_{ij}$ is the Euclidean distance between mass changes in an M element MOF array adsorbing either gas mixture i or gas mixture j based on the following equation:

$$m_{ij} = \sqrt{\Sigma_{k=1}^{M}(m_{k,i}-m_{k,j})^2}$$

9. The method of claim 8, further comprising:
using the SAGS score as the effectiveness score;
selecting the potential array with the highest effectiveness score; and
fabricating the selected potential array.

10. The method of claim 7, wherein the plurality of gas mixtures are selected by selecting a plurality of gas components and varying each of the gas components in concentrations from 0-1 mole fractions in a predetermined step size to generate the plurality of gas mixtures, and
wherein calculating the effectiveness score for each of the potential arrays comprises:
selecting a subset of the plurality of gas mixtures;
simulating adsorption characteristics of each of the MOF materials for each gas mixture in the subset of the plurality of gas mixtures;
for each of the MOF materials and each of the subset of the plurality of gas mixtures, calculating a probability distribution of the gas mixture from the subset of the plurality of gas mixtures being selected gas mixtures from the plurality of gas mixtures;
for each of the potential arrays, combining the probability distributions for each of the MOF materials in the potential array; and
calculating a Kullback-Liebler divergence (KLD) for each gas mixtures in the subset of the plurality of gas mixtures for each of the potential arrays using the following equation:

$$KLD = \sum_{i}^{N} P_i \log\frac{P_i}{Q_i}$$

where a probability at each mole fraction is represented by $P_i$, and a reference probability of $Q_i$ is a probability equivalent to 1/N, where N is the predetermined step size divided by 1.

11. The method of claim 10, further comprising:
calculating an average KLD by taking the average of the KLD calculated for each of the gas mixtures in the subset of the plurality of gas mixtures.

12. The method of claim 11, further comprising:
using the calculated average KLD as the effectiveness score;
selecting the potential array with the highest effectiveness score; and
fabricating the selected potential array.

13. The method of claim 10, wherein the subset of gas mixtures includes a single gas mixture, wherein the method further comprises:
using the calculated KLD as the effectiveness score;
selecting the potential array with the highest effectiveness score; and
fabricating the selected potential array.

* * * * *